Figure 1:
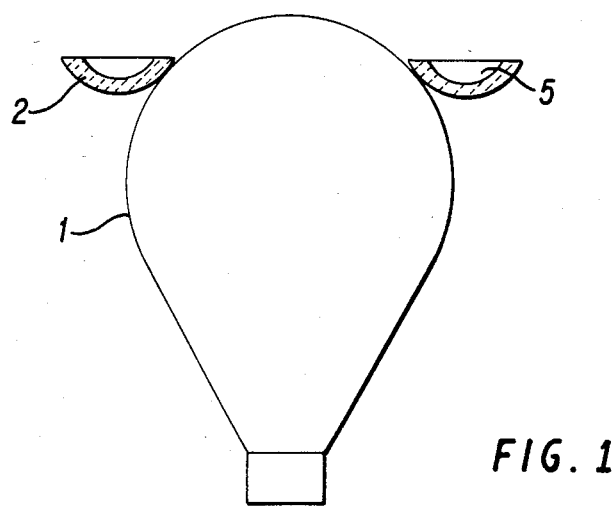

United States Patent [19]
Gyulay

[11] Patent Number: 4,579,717
[45] Date of Patent: Apr. 1, 1986

[54] AIR FRESHENER

[76] Inventor: Joseph Gyulay, P.O. Box 81361, Cleveland, Ohio 44181

[21] Appl. No.: 616,689

[22] Filed: Jun. 4, 1984

[51] Int. Cl.$^4$ .............................................. A62B 7/08
[52] U.S. Cl. ................................... 422/125; 422/305
[58] Field of Search .......................... 422/4, 120–126, 422/305

[56] References Cited

U.S. PATENT DOCUMENTS

| | | | |
|---|---|---|---|
| 1,403,548 | 1/1922 | Gudeman | 422/125 |
| 1,556,680 | 10/1925 | Dorment | 422/125 |
| 2,124,543 | 7/1938 | Clyne | 422/305 |
| 2,539,696 | 1/1951 | Morrison | 422/125 |

Primary Examiner—Barry S. Richman
Assistant Examiner—Titus B. Ledbetter, Jr.
Attorney, Agent, or Firm—Ralph Hammar

[57] ABSTRACT

A room air freshener in the form of a porous ceramic ring sized to rest on the upper end of a conventional electric lamp bulb. The ring has a cavity in its top surface of volume less than the combined volume of the pores of the ceramic so that a fragrant oil filling the cavity will be completely absorbed by the ceramic leaving a dry outer surface which does not collect dust. When the lamp bulb is turned on, the ring is heated to vaporize the oil and release the fragrance which permeates the room.

1 Claim, 2 Drawing Figures

U.S. Patent  Apr. 1, 1986  4,579,717

AIR FRESHENER

In the prior art, asbestos rings saturated with fragrant oil and annular metal rings containing a fragrant oil have been mounted on electric lamp bulbs. The asbestos rings collected dust and could not be cleaned. The metal rings were hazardous because tipping of the lamp could spill hot oil.

This invention eliminates the problems of the prior art by a porous ceramic ring which absorbs the fragrant oil so that when cooled, the outer surface of the ring is dry and does not collect dust. When the lamp bulb is turned on, the ceramic, being an insulator, is heated to a relatively low temperature compared to the outer surface of the lamp bulb, but sufficient to vaporize the absorbed oil and release the fragrance.

Figure 2:
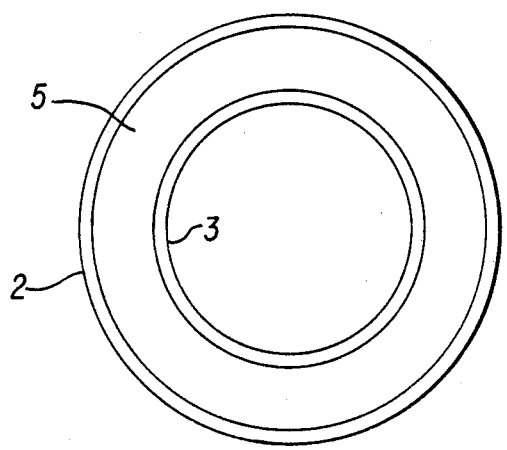

In the drawing,

FIG. 1 is an elevation of a small lamp bulb on which a porous ceramic ring impregnated with fragrant oil is mounted, and FIG. 2 is a top plan view.

In the drawing, 1 indicates a conventional 25 watt lamp bulb. Lamp bulbs of larger size, such as 40 watt, 60 watt, etc., may be used, but are not necessary. On the upper end of the lamp bulb is an annular porous ceramic ring 2. The inside diameter 3 of the ring is smaller than the maximum outside diameter of the lamp bulb so that the ring merely rests on top of the lamp bulb and is received in stable supporting relation. It is not necessary that the supporting surface of the ceramic ring be circular, as shown. Any regular polygonal shape could be used. A circle can be considered to be a polygon of an infinite number of sides. Also, the inner surface of the ring might have feet for making supporting engagement with the lamp bulb.

As is apparent from the radial section through the ceramic body, the combined volume of the pores of the body is greater than the volume of the cavity 5 in the upper surface of the body. This insures that an initial filling of the cavity 5 with fragrant oil will be completely absorbed in the ceramic body. The outer surface of the ceramic body is therefore dry and is not a dust catcher. However, if dust should settle on the ring, it can easily be removed. If the cavity after being first filled with oil were given a second filling before any of the first filling had been used, there would be the possibility of exceeding the absorbing capacity of the ceramic ring, in which case unabsorbed or excess oil would remain in the cavity and the hydrostratic head of this oil would cause drops to collect on the under surface of the ring. When this condition is observed, wiping the ring with paper toweling will quickly correct the overfill condition. Since the liquid is absorbed in ceramic, mounting with the concave side up is not necessary. The ring works equally well when inverted.

When the lamp bulb is off, the ceramic ring does not release appreciable fragrance to the room. The ceramic ring does not interfere appreciably with the light emission of the lamp bulb and can be left in place for long periods of time with the lamp bulb off when no fragrance emission is desired.

The volume of fragrant oil absorbed by the ceramic is nearly equal to a large fraction of the volume of the ceramic.

I claim:

1. An annular porous ceramic ring received in supporting and heat receiving relation on an electric lamp bulb, said ring having at its inside diameter a lamp bulb engaging supporting structure lying on a circle of diameter less than the maximum outside diameter of the lamp bulb so said ring may be received on the upper end of the lamp bulb, said ring having a cavity for ease in impregnating the ring with fragrant oil, the pores of the ring having a combined volume sufficiently greater than the volume of the cavity so all of the fragrant oil that fills the cavity is absorbed by the ring when said ring is cold leaving a dry outer surface on said ring which does not collect dust and can easily be wiped clean and does not release appreciable fragrance while the ring is cold, said ring being heated by the lamp bulb to vaporize the absorbed oil and freshen the air, said ring being sized so it does not interfere appreciably with light transmission from the lamp bulb.

* * * * *